United States Patent [19]

Ruff

[11] Patent Number: 4,727,885
[45] Date of Patent: Mar. 1, 1988

[54] SELF APPLIED BLOOD PRESSURE CUFF

[75] Inventor: Gray E. Ruff, Hillsboro, Oreg.

[73] Assignee: SpaceLabs, Inc., Bothell, Wash.

[21] Appl. No.: 946,471

[22] Filed: Dec. 24, 1986

[51] Int. Cl.$^4$ .............................................. A61B 5/02
[52] U.S. Cl. .................................... 128/686; 128/327
[58] Field of Search ............... 128/672, 677, 686, 327, 128/402–403

[56] References Cited

U.S. PATENT DOCUMENTS

| | | | |
|---|---|---|---|
| 3,654,931 | 4/1972 | Haglewood | 128/327 |
| 3,659,592 | 5/1972 | Natkanski | 128/686 |
| 3,669,096 | 6/1972 | Hurwitz | 128/686 |
| 3,752,148 | 8/1973 | Schmalzbach | 128/686 |
| 4,353,374 | 10/1982 | Rebbe et al. | 128/686 |
| 4,354,503 | 10/1982 | Golden | 128/686 |
| 4,429,699 | 2/1984 | Hatschek | 128/681 |
| 4,465,076 | 8/1984 | Sturgeon | 128/686 |
| 4,527,566 | 7/1985 | Abare | 128/402 |
| 4,548,249 | 10/1985 | Slaughterbeck | 128/686 X |

FOREIGN PATENT DOCUMENTS 0949352 6/1974 Canada .
2220233 5/1978 Fed. Rep. of Germany .

Primary Examiner—Kyle L. Howell
Assistant Examiner—Angela D. Sykes
Attorney, Agent, or Firm—Seed and Berry

[57] ABSTRACT

A self applied blood pressure cuff particularly for use with ambulatory blood pressure products and suitable for use on either the left or right limbs of the patient is disclosed. The cuff includes an elongated, flexible band having a body side face and an outward face and a compartment. It further includes an inflatable bladder having a portion adapted to protrude through one of two openings in the band when the bladder is on either the left or right arm. The two openings are located opposite one another on opposite lengthwise edges of the band. First and second indicia placed adjacent the openings on the outward face of the band identify the position of the protruding portion for use on either the left or right arm.

6 Claims, 5 Drawing Figures

SELF APPLIED BLOOD PRESSURE CUFF

BACKGROUND OF THE INVENTION

The present invention relates to blood pressure cuffs used for taking blood pressure measurements, more particularly, to self applied cuffs used with the arms of human patients.

Blood pressure cuffs are well known in the prior art and comprise an elongated flexible band having a predetermined length and width, a body side face and an outward face. The band is adapted to be wrapped around a limb, such as an arm or leg, to measure blood pressure. Attachment means such as VELCRO TM is provided with the band to hold the band on the limb. Some self applied cuffs include a buckle to which one end of the band is attached and through which the other end of the band is passed to form a sleeve.

The front and back faces of the band are joined together around their peripheries to form a compartment into which an inflatable bladder is inserted. A hose portion coupled to the bladder and usually integrally formed therewith extends out from the compartment through an opening in the periphery.

When wrapping the band around the arm, it is desirable for accuracy of measurement that the center of the bladder be located over the brachial artery on the inner side of the upper arm. It has been found most convenient in ambulatory measurement applications when wrapping the band around the arm that the hose portion extend through a top periphery or edge of the cuff such that a hose coupled between the cuff and monitoring device is then routed up the front of the arm across the back of the neck to the other side of the body to the monitoring device which is usually strapped to the patient's waist. In order to accomplish this the slot in the periphery of the cuff is offset from the center of the bladder and located solely on one side thereof so that the hose portion of the bladder extends along the front of the arm. Prior art cuffs of which the inventor is aware have only a single opening offset as described above. When applying a self-applied cuff to an arm of a patient, e.g. the left arm, it has been found most convenient to insert a tapered end of the cuff through the buckle of the cuff at the opposite end with the fastener material on one face of the cuff facing out. This forms a sleeve into which the arm is inserted. To tighten the cuff, the user reaches under the inserted arm and pulls the tapered end of the cuff away from the body trunk. Then the cuff is pulled over the buckle toward the trunk and the loop and hook fastener material is pressed together. If the user now attempts to use the cuff on the other arm, i.e. the right arm, in order to align the bladder and hose portion as described above, the user must tighten the cuff by first pulling the band toward the trunk and then folding the band over the buckle away from the trunk to attach the band. This is less convenient and more difficult for the user.

It is desirable therefore to provide a single self applied cuff design which is suitable for use on either arm.

SUMMARY OF THE INVENTION

The present invention relates to a self applied blood pressure cuff adapted for use on either the left or right arm of the body. It comprises a band having a body side face and an outward face and a compartment. The compartment is open to ambient atmosphere through at least a pair of openings on opposite lengthwise edges of the band. The cuff further includes an inflatable bladder adapted to be removably confined within the compartment. The bladder includes a portion which protrudes from the compartment through one of the openings.

In the preferred embodiment, the openings are formed at the periphery of the two faces of the band where the faces are joined together. The protruding portion extends through a first opening of the pair when the bladder is on the left arm and through a second opening when the bladder is on the right arm. First and second indicia are placed on the outward face adjacent the first and second openings, respectively, to identify which is to be used for the right and left arms. A third indicia identifying the centerline of the bladder for placement along the brachial artery is also provided on the outward face of the band.

The cuff further includes hook-like fastener material on a first area of the outward face near one end of the band with loop-like fastener material on a second area of the outward face adjacent the first area.

DETAILED DESCRIPTION OF THE DRAWINGS

Figure 1:
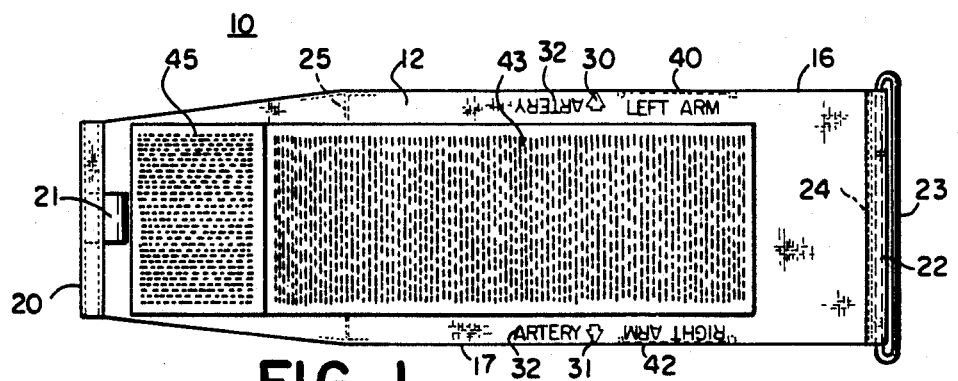
FIG. 1 is a planar elevational view of the outside face of a band portion of the preferred embodiment blood pressure cuff of the present invention.
Figure 2:
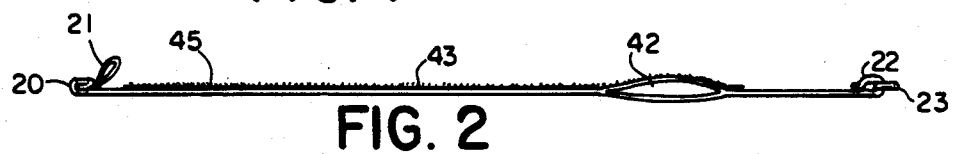
FIG. 2 is a view of a first lengthwise edge of the band portion of FIG. 1
Figure 3:
FIG. 3 is a view of a second lengthwise edge of the band portion of FIG. 1.
Figure 4:
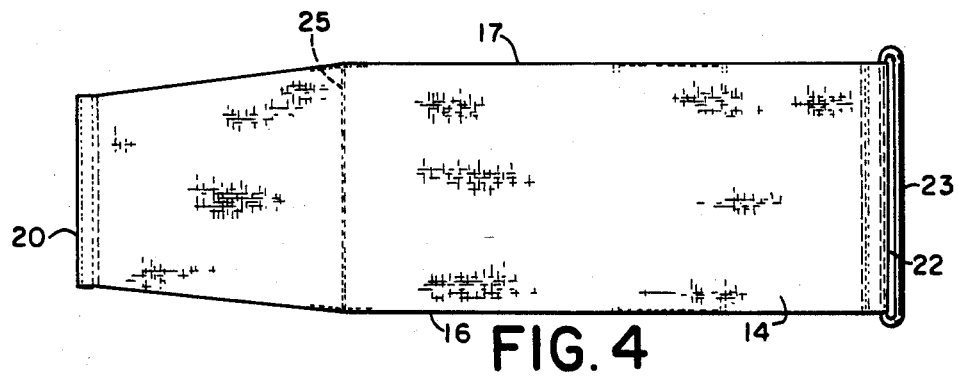
FIG. 4 is a body side planar elevational view of the band portion of the cuff of FIG. 1.
Figure 5:
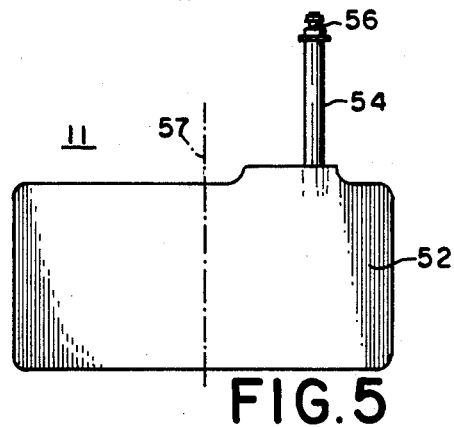
FIG. 5 is a planar elevational view of an inflatable bladder portion of the cuff for use with the band portion of FIGS. 1 through 4.

Referring now to the figures, there is shown a blood pressure cuff comprising an elongated flexible band designated generally 10 having an overall length L with width W along most of its length. The cuff further includes the inflatable bladder designated generally 11 in FIG. 5. The band comprises an outward face 12 in FIG. 1 and a body-side face 14 in FIG. 2 which are joined together along their lengthwise edges 16 and 17. The faces may be made of any suitable fabric or material such as nylon or a polyester cotton blend. In the preferred embodiment, the faces are sewn together along their lengthwise edges.

The lengthwise edges 16 and 17 taper in width from their maximum width toward the end 20 of the band 10 which is formed by folding the tapered ends of the faces over a couple of times and stitching them together. A loop of material 21 which provides a finger hold for handling the cuff is attached at the folds.

At the opposite end 22 of the band, the ends of the faces wrap around an oval metallic buckle 23 and are stitched along line 24 to attached the buckle to the band. The two faces are sewn together across their width along dotted line 25 located at a spot where the taper starts. This creates a compartment in the band opposite the tapered end, the compartment formed by dotted line 25, portion of lengthwise edges 16 and 17, end 22 and portions of the two faces 12 and 14.

Two oppositely directed arrows 30 and 31 lying along a common straight line perpendicular to lengthwise edges 16 and 17 with the word ARTERY 32 adjacent is printed or placed on the outward face 12 of the band 10. Arrow 30 points to and is adjacent thereto the lengthwise edge 16, while arrow 31 points to and is adjacent lengthwise edge 17. The arrows point to a spot near the halfway point between end 22 and stitch line 25 but closer to the end 22 than stitch line 25.

Two equally sized openings 40 and 42 are provided between the two faces, one along edge 16 and one along edge 17. The openings 40 and 42 are located adjacent arrows 30 and 31, respectively, and intermediate the arrows and end 22. The faces 12 and 14 can be spread apart at the openings to gain access to the interior of the compartment.

Just below the slot 40 the words LEFT ARM are printed or placed on the outward face 12 of the band while the words RIGHT ARM are printed or placed on face 12 just below the slot 42.

In the preferred embodiment a band suitable for use on adults is 18.00 inches long and a maximum of 5.80 inches wide tapering at edge 20 to 4.25 inches. The dotted line 25 is parallel to and spaced apart by 12.00 inches from end edge 22. Each slot 40 and 42 is 2.5 inches long beginning 3.50 inches from the end 22 and continuing toward the opposite end 20.

The outward face 12 of the band is provided with a rectangularly shaped region of loop fastener material 43 usually made of nylon. A suitable material is that which is sold under the trademark VELCRO TM. In the preferred embodiment a 12 to 18 per inch zig-zag stitch is used. The loop material covers an area 4 inches wide by 11 inches long starting near the end 22 and running lengthwise along the face 12. A mating-hook portion of fastener material 45, covering an area of 4 inches by 3 inches, is provided on the face 12 starting near edge 20.

The bladder 11 is made from an inflatable rubber material and comprises a main chamber portion 52 and an integrally formed hose 54 with a barbed nipple connector 56 at its distal end, the hose open to the interior of chamber portion 52 where it joins therewith. In the preferred embodiment the bladder is 4.9 inches wide and 10.25 inches long with the hose located 3.75 inches from one end.

The bladder is foldable and can be inserted into and removed from the compartment of the band through either of openings 40 or 42. When positioned within the compartment the centerline of the bladder 57 lies coaxial with either arrows 30 and 31 and the hose will extend out of the compartment through either opening 40 or 42.

When in use the bladder is placed within the compartment with the hose extending out from one of the openings 40 or 42 depending on the arm to be used. With face 14 disposed to engage the arm, the band is positioned between the patient's arm and chest wall so that the arrow lies along the brachial artery on the inside of the arm.

As described earlier, if the band is to be placed on the left arm, the bladder is placed in the compartment with hose portion 54 extending out from opening 40. With face 12 facing outwardly end 20 is inserted through the loop 23 to form a sleeve. The left arm is inserted into the sleeve with the arrow 30 next to the words LEFT ARM lying along the brachial artery on the underside of the arm and with the hose portion 54 extending upwardly along the front of the arm. Grabbing the loop 21 with the right hand placed under the left arm the band is pulled away from the body, folder over the loop 23 and pulled toward the body. The hook material is pressed against the loop material to fix the band on the left arm.

If it is now desired to use the cuff on the right arm, the bladder is removed from the compartment and reinserted with the hose portion 54 extending out through opening 42. The above self application procedure is then repeated. If separate openings were not present on opposite lengthwise edges, it would not be possible to apply the cuff to either arm with the hose portion pointing upwardly and still apply in the manner described above. On at least one arm it would be necessary after forming the sleeve and inserting the arm, to first pull the loop 21 under the arm toward the trunk to tighten and then fold the band over the buckle away from the trunk. This is a more difficult procedure.

What is claimed is:

1. A self applied blood pressure cuff adapted to be positioned on an arm of a body comprising:
    an elongated flexible band having first and second ends, a buckle attached to said second end of said band, said band having a body side face intended for engagement with the arm and an outward face joined together with the body side face along lengthwise edges, said band having a compartment therein which is partially open to ambient atmosphere through a pair of openings in said band, each of said openings located opposite one another on opposite lengthwise edges; and
    an inflatable bladder adapted to be removably confined within said compartment, said bladder having a portion protruding out from said compartment through one of said openings, said protruding portion protruding through a first one of said openings when said cuff is to be applied to a left arm and through a second one of said openings when said cuff is to be applied to a right arm.

2. The blood pressure cuff of claim 1 wherein said cuff further comprises first and second indicia means placed on said outward face adjacent said first and second openings, respectively, to identify which of said openings should be used for said bladder protruding portion when said cuff is to be applied to said left and said right arms.

3. The blood pressure cuff of claim 2 wherein said cuff further comprises third indicia means on said outward face for indicating the approximate location of said centerline of said bladder confined within said compartment for aligning said centerline in the proper position on said arm.

4. The blood pressure cuff of claim 3 wherein said blood pressure cuff is adapted for use on the arm of said patient with an ambulatory blood pressure monitor and said first and second indicia means identify the right and left arm, respectively.

5. The blood pressure cuff of claim 4 wherein said third indicia means refers to the brachial artery of the arm.

6. The blood pressure cuff of claim 1 wherein said cuff further comprises:
    hook-like fastener material on a first area of said outward face adjacent said first end and loop-like fastener material on a second area of said outward face adjacent said first area for mating engagement with said hook-like fastener material.

* * * * *